(12) United States Patent
Dry et al.

(10) Patent No.: US 10,912,916 B2
(45) Date of Patent: Feb. 9, 2021

(54) ELECTRONIC DISPLAY ADJUSTMENTS TO MITIGATE MOTION SICKNESS

(71) Applicant: Ford Global Technologies, LLC, Dearborn, MI (US)

(72) Inventors: Alan Dry, Grosse Pointe Woods, MI (US); Jimmy Moua, Canton, MI (US); Johnathan Andrew Line, Northville, MI (US); Marcos Silva Kondrad, Macomb Township, MI (US); Kevin Preuss, Berkley, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 332 days.

(21) Appl. No.: 16/107,603

(22) Filed: Aug. 21, 2018

(65) Prior Publication Data
US 2020/0061332 A1    Feb. 27, 2020

(51) Int. Cl.
*A61M 21/02* (2006.01)
*G06F 3/01* (2006.01)
*A61M 21/00* (2006.01)

(52) U.S. Cl.
CPC ............. *A61M 21/02* (2013.01); *G06F 3/011* (2013.01); *A61M 2021/005* (2013.01)

(58) Field of Classification Search
USPC .................................................. 600/26–28
See application file for complete search history.

(56) References Cited

U.S. PATENT DOCUMENTS

| 6,497,649 | B2 | 12/2002 | Parker et al. |
| 7,128,705 | B2 | 10/2006 | Brendley et al. |
| 2015/0290453 | A1 | 10/2015 | Tyler et al. |

FOREIGN PATENT DOCUMENTS

EP    3167927 A1    5/2017

OTHER PUBLICATIONS

Anti Motion Sickness App 2.9. https://anti-motion-sickness-app.soft112.com/download.html.
Bos, et al., "A theory on visually induced motion sickness," Displays, 2008, vol. 29, Issue 2, pp. 47-57.

*Primary Examiner* — John P Lacyk
(74) *Attorney, Agent, or Firm* — Brandon Hicks; Eversheds Sutherland (US) LLP

(57) ABSTRACT

Systems, methods, and computer-readable media are disclosed for automatic display modifications to avoid motion sickness. Example methods may include determining a first acceleration value of a device in a first direction, determining a first acceleration vector using the first acceleration value, and determining a baseline location of a focal point of a display of the device. Some embodiments may include determining a first adjusted location of the focal point of the display based at least in part on the first acceleration vector, and causing presentation of a graphical indicator of the first adjusted location of the focal point at the display, where the graphical indication is positioned at a second direction relative to the baseline location, and the second direction is opposite the first direction.

19 Claims, 9 Drawing Sheets

ELECTRONIC DISPLAY ADJUSTMENTS TO MITIGATE MOTION SICKNESS

TECHNICAL FIELD

The present disclosure relates to systems, methods, and computer-readable media for systems and methods to adjust electronic displays to mitigate motion sickness.

BACKGROUND

Certain people may experience motion sickness while in a moving vehicle. Motion sickness may be caused by, or aggravated by, focusing of a user's eyes on an object. For example, use of an electronic device or reading a book or other written material may exacerbate or cause motion sickness while a user is in a vehicle. Motion sickness may be a result of poor posture and/or a difference in perceived vertical between that of a user's inner ear and an actual vertical, which may be impacted by acceleration or deceleration of a vehicle. However, people may desire to use electronic devices or consume written material while in a moving vehicle.

DETAILED DESCRIPTION

Figure 1:
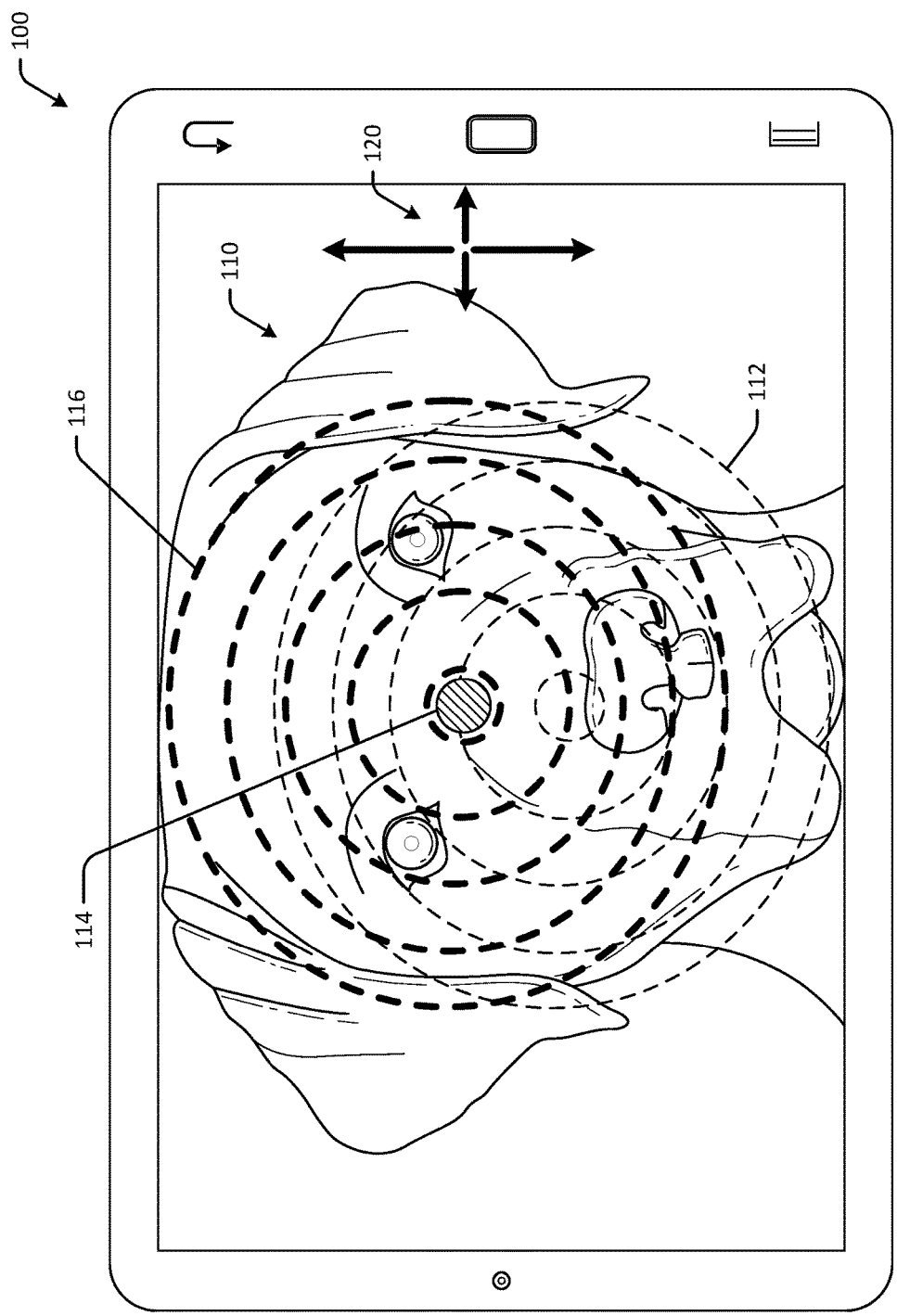
FIG. 1 is a schematic illustration of an example implementation of adjusting electronic displays to mitigate motion sickness in accordance with one or more embodiments of the disclosure.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ certain embodiments of the disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for certain applications. Various combinations and modifications of the features consistent with the teachings of this disclosure, however, could be desired for particular applications or implementations.

Embodiments of the disclosure are directed to systems and methods to mitigate motion sickness for users in vehicles, such as automobiles, planes, trains, etc. Some embodiments may include software components that generate graphical indicators and/or grid patterns on a display of a device that help adjust a focal point of a user's eyes, which may reduce a likelihood of experiencing motion sickness and/or mitigate symptoms of motion sickness that may be experienced by users in vehicles. Some embodiments may include projection systems that can be used to project graphical indicators and/or grid patterns on reading materials, such as books, magazines, newspapers, and so forth. Projection systems may be included in a user device, such as a smartphone, or may be attached to the interior of a vehicle, such as at a vehicle headliner.

To mitigate motion sickness, embodiments of the disclosure may determine a difference between a true perpendicular direction (e.g., an actual location of a horizon, etc.) and a perceived perpendicular direction of a user (e.g., the perceived location of the horizon by the inner ear of the user, etc.), which may be impacted by acceleration and/or other motion of a vehicle. The difference may be determined using acceleration data from one or more sensors, such as one or more accelerometers of a user device (e.g., smartphone, smartwatch, etc.) and/or one or more sensors of a vehicle. The determined acceleration value using the one or more sensors may be converted to a vector and may incorporate a direction of acceleration, and may be used to determine a positioning of a graphical indicator for presentation on a display of a user device or other physical reading material. The acceleration may be continuously determined and positioning of the graphical indicator may be adjusted continuously or by using an iterative process (e.g., a process executed every 5 seconds or another desired time interval, etc.).

The graphical indicator may be used as a focal point for the user's eyes. For example, if the vehicle and/or user device is determined to be accelerating in a forward direction, the graphical indicator may be positioned further up or higher on the display of the device than a center point of the display. The graphical indicator may be, in one example, a dot or solid circle. Any suitable geometry may be used. The graphical indicator may have a certain color, such as yellow. In some instances, the color of the graphical indicator may be determined based at least in part on other content displayed on the device display, so as to ensure contrast. For example, if the majority color of content displayed on the display of the device is black, the graphical indicator may be yellow or white, whereas if the majority color of content displayed on the display of the device is white, the graphical indicator may be black, gray, or another relatively dark color. The graphical indicator may be presented as an overlay over the content and may be presented continuously (e.g., while acceleration is detected, etc.), or may be presented for a certain length of time, such as 5 seconds or another time interval. The graphical indicator may have some translucency, such as about 50% in some instances to allow a user to view content that may be underneath the graphical indicator.

In some embodiments, a grid pattern, such as a pattern of one or more concentric circles, may be at least partially presented about the graphical indicator. For example, the grid pattern may be disposed about the graphical indictor so as to highlight the location of the graphical indicator. In some embodiments, the grid pattern may include solid or dashed lines, or a combination thereof, and/or lines of different weights, that form one or more circles about the graphical indicator. The grid pattern may be presented for the same length of time as the graphical indicator or for a length of time that is less than the length of time the graphical indicator is presented.

The grid pattern and graphical indicator may be presented in addition to a baseline grid pattern. The baseline grid pattern may be a previous location of the graphical indicator, or may be a center of the display, which may be a natural focal point for the user's eyes.

The graphical indicator, and optionally the grid pattern and/or the baseline grid pattern, may be presented at the display or written material as vehicle acceleration or deceleration (negative acceleration) is detected. In some embodiments, a sensitivity threshold may be implemented so as to avoid presentation of the graphical indicator (and grid pattern/baseline grid pattern) in instances where acceleration is low or gradual, as the user may not to adjust a focal point of the user's eyes in such instances because the risk of motion sickness may be relatively low.

Some embodiments may be implemented using a device software component, while other embodiments may be implemented using a vehicle software component and/or remote server software component.

Embodiments may therefore reduce or eliminate input contradictions to a user's brain from the user's eyes and the canals of the user's inner ear. The alignment of visual and perceived verticals may satisfy the user's brain need for agreement in balance related inputs to reduce or avoid motion sickness.

FIG. 1 is a schematic illustration of an example implementation of adjusting electronic displays to mitigate motion sickness in accordance with one or more embodiments of the disclosure. Although the example of FIG. 1 illustrates a device, other embodiments may include a vehicle and/or remote server that perform one or more operations. Example architecture is described with respect to at least FIG. 9.

Embodiments of the disclosure include systems and methods for generating graphical indicators or other visually perceptible elements for presentation on displays or written materials that may mitigate motion sickness. Some embodiments may use one or more electronic displays, while other embodiments may use projector systems and/or vehicle components.

Some vehicle passengers who use electronic devices, cell phones, laptops, or read books, magazines, newspapers, etc. while in a moving vehicle experience motion sickness. Vehicle passengers who read or use electronic devices often do so in a head down posture. When a vehicle passenger looks down at their lap for an extended period it can cause loss of the visual horizon, which can be perceived by looking out a window in one example. Loss of the visual horizon can cause motion sickness. The user or passenger's inner ear naturally gives a perception of what direction is true vertical based at least in part on perceived movement of the user's body. This perception may be referred to as the inner ear perpendicular. Similarly, the user or passenger's eyes concurrently give a perception of what direction is true vertical based at least in part on what the person is seeing. When there is a difference in perception of vertical between the inner ear and eyes, motion sickness may result.

One reason that there may be a difference in perception of vertical between a person's eyes and inner ear when looking down in a vehicle may be because the eyes believe the body is stationary, but the inner ear knows the body is moving. Meanwhile, the eyes of the user are focused on a book or electronic device, which is usually stationary on the person's lap or in the person's hand. This can cause the user's eyes to signal the brain that the person is not in motion. However, the inner ear does not rely on vision and is generally based at least in part on balance and equilibrium, and can determine that the car is accelerating. Therefore, conflicting signals are sent to the brain from the eyes and inner ear. This leads to a difference in what direction is perceived as true vertical and the user can experience motion sickness.

As illustrated in FIG. 1, embodiments of the disclosure may include a software application that can be executed on a device that assists in eliminating input contradictions to the brain from the user's eyes and inner ear to eliminate or mitigate motion sickness. The application may generates a solid line grid for display on the display of the passenger's electronic device to provide a visual representation of the inner ear's perception of vertical. The application may also generate a second dotted line grid on the display of the electronic device that represents what true vertical would be if the vehicle were stationary. The second dotted line grid represents what the passenger's eyes perceive as true vertical since they are focused on the stationary electronic device or book. The two grids can overlap, with the vertical solid line grid on top of the dotted line grid for a stationary vehicle. These overlapping grids have a subliminal effect on the brain and help satisfy the need for agreement between the inputs from eyes and inner ear. When viewed by the user, the user's eyes may subliminally follow the solid line grid showing the perceived inner ear vertical, creating agreement in the signals sent to the brain.

The electronic device may be configured to calculate the perceived inner ear vertical using one or more accelerometers. By knowing the acceleration due to the movement of the vehicle using the device's accelerometer, and by optionally calculating the force of gravity on the vehicle, the application may calculate the resulting perceived inner ear perpendicular. The application may then cause a grid to be displayed on the display of the electronic device.

The application may execute in a background of the device operating system in some embodiments, and may generate the grid pattern(s) for display whenever the perceived inner ear vertical contradicts the visual vertical by a certain amount. For example, to eliminate excessive display when minimal accelerations are present, the grid may be displayed when the acceleration is above a sensitivity threshold value.

If the passenger is reading a book or magazine or other material, a projector can be used to project the grid pattern(s) onto the material. The projector can project the grid pattern(s) onto the book or magazine to help eliminate signal contradictions from the eyes and inner ear. A projector could either be attached to a smartphone, mounted somewhere in the vehicle, or may otherwise be in communication with the device and/or vehicle.

In some embodiments, biometric feedback can be generated for the user, which may indicate the number of occasions in a given time period which could have caused motion sickness, and the user can therefore determine the benefit provided by the software application (e.g., the user didn't experience any of 4 possible instances of motion sickness, etc.).

In FIG. 1, a user device 100 may be configured to generate grid patterns so as to reduce or avoid motion sickness in accordance with one or more embodiments of the disclosure. The user device 100 may include one or more software components, such as acceleration components and/or display adjustment components illustrated in FIG. 9, configured to generate graphical indicators and/or grid patterns for presentation on a display 110 of the user device 100. The user device 100 may include one or more sensors, such as an accelerometer. Based at least in part on output from the accelerometer or other sensor, the user device 100 may determine that the user device 100 is in a vehicle that is accelerating. For example, certain magnitudes of acceleration may be associated with movement in a vehicle, as opposed to, for example, acceleration that may be a result of a person jogging, etc.

The user of the user device 100 may be using the user device 100 to consume content, such as text or video content. The acceleration may potentially cause the user motion sickness. Accordingly, the user device 100 may determine a direction and magnitude of the acceleration. In some embodiments, the lateral, longitudinal, and or compound two-dimensional acceleration may be determined by the user device 100. For example, the accelerometer of the user device 100 may output the lateral, longitudinal, and or compound two-dimensional acceleration. One or more software components at the user device, such as an acceleration component, may determine a clock face vector that can be used to correct a perceived vertical, as discussed with respect to FIGS. 3-4. The user device 100, such as a display adjustment component, may generate a baseline grid, one or more graphical indicators, and one or more correction patterns using the clock face vector. The generated grid pattern may be overlaid on content presented at the display 110.

In the illustrated embodiment of FIG. 1, a baseline grid pattern 112 may be generated and may be indicate a previous and/or central focal point for a user's eyes. For example, in FIG. 1, the baseline grid pattern 112 may be slightly below a central point along a vertical axis of the display. The baseline grid pattern 112 may be represented using one or more circles, such as concentric circles, with dashed and/or solid lines and may have a line weight of a first value.

The user device 100 may determine that acceleration is detected in a forward direction (relative to the user device 100), and may therefore determine that the focal point of the user's eyes should be further upwards on the display 110, where upwards is relative to a previous position as indicated by the baseline grid pattern 112.

Accordingly, the user device 100 may generate a graphical indicator 114 that displays a focal point for the user's eyes. The user may subliminally adjust the focus of their eyes to the graphical indicator 114, and may therefore avoid or mitigate a feeling of motion sickness.

A grid pattern 116 may optionally be generated about the graphical indicator 114. The grid pattern 116 may include one or more circles, such as concentric circles, and may have dashed or solid lines. The grid pattern 116 may have a line weight of a second value that is greater than the first value of the baseline grid pattern 112. This may help improve visibility by the user.

As the device 100 detects acceleration in different directions and in different magnitudes, the graphical indicator 114 and/or grid pattern 116 may move in a different direction, such as an opposite direction, relative to the direction of acceleration. The amount of movement may be proportional to the magnitude of acceleration, as detected by one or more accelerometers of the user device 100.

Accordingly, the graphical indicator 114 and/or the grid pattern 116 may move in directions 120 (although four directions are illustrated, any direction and any magnitude may be used) responsive to acceleration detected by the device 100 or by another system in communication with the device 100, such as a vehicle component or system.

The graphical indicator 114, grid pattern 116, and/or baseline grid pattern 112 may be presented for a certain duration, such as during acceleration or for a short time thereafter (e.g., 5 seconds after acceleration stops, etc.), or until the user indicates presentation is no longer desired, such as by selecting an input at the user device 100.

The color of the graphical indicator 114 and/or lines of the grid pattern 116 and baseline grid pattern 112 may be determined based at least in part on colors of content presented at the display 110. For example, if the dog illustrated in FIG. 1 is black, the graphical indicator 114 may be yellow or white, or another relatively light color, so as to provide contrast for the user to easily identify the location of the graphical indicator 114. The graphical indicator 114 may be translucent in some embodiments, so as to allow users to view content underneath the graphical indicator 114.

The graphical indicator 114 and/or the grid pattern 116 may simulate the perceived perpendicular of the canals of the inner ear of the user of the user device 100 and display it on the display 110 using a grid pattern. This may reduce or eliminate input contradictions to the brain from eyes and canals of the inner ear, thereby reducing or avoiding motion sickness. The grid pattern 116 may be a visual representation of the inner ear of the user's perception of vertical. The alignment of visual and perceived verticals may satisfy the brain's need for agreement in balance related inputs to quell motion sickness.

The graphical indicator 114 and/or grid pattern 116 may serve to duplicate the output of the inner ear of the user. The graphical indicator 114, grid pattern 116, and/or baseline grid pattern 112 may remain presented together for a length of time, such as about one second, after which the baseline grid pattern 112 may fade centering the visual attention in the remaining, yet displaced graphical indicator 114 and/or and grid pattern 116. In some instances, such as instances of high changes in acceleration, the baseline grid pattern 112 and/or grid pattern 116 may not be generated, and only the graphical indicator 114 may be generated.

Accordingly, embodiments of the disclosure include systems and methods to avoid or mitigate motion sickness using one or more software components to generate graphical indicators and/or grid patterns on a display of a device and/or using a projector system to generate a projected image on written material.

Figure 2:
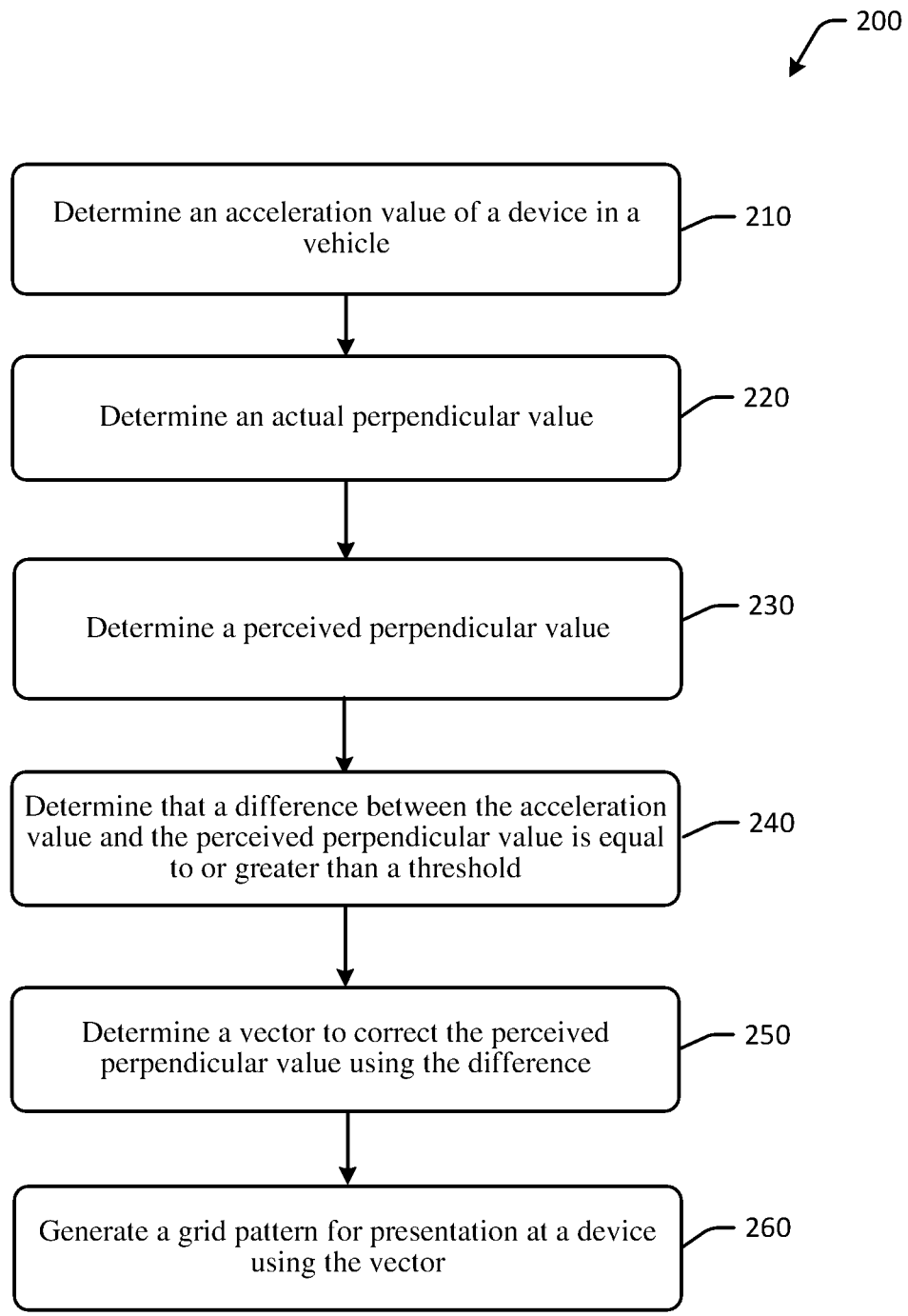
FIG. 2 is a schematic illustration of an example method for adjusting electronic displays to mitigate motion sickness in accordance with one or more embodiments of the disclosure.

FIG. 2 is a flow diagram of an example process flow 200 for adjusting electronic displays to mitigate motion sickness in accordance with one or more embodiments of the disclosure. Some of the blocks of FIG. 2 represent operations that may be performed or executed by an acceleration component and/or display adjustment component, such as that illustrated in FIG. 9. In some embodiments, the operations may be performed in a distributed manner across a plurality of computer systems. Portions of FIG. 2 are discussed in conjunction with FIGS. 3-4.

Block 210 of the process flow 200 may include determining an acceleration value of a device in a vehicle. For example, a user device may determine an acceleration value using one or more inertial sensors, such as an accelerometer, that may be coupled to the user device and/or may be coupled to a computer system in communication with the user device. For example, the accelerometer may be at a vehicle that is in wired or wireless communication with the user device. The acceleration value may be an absolute value, or may include a direction. Deceleration may be represented as a negative acceleration value. In some embodiments, acceleration values may be combined with other sensor data, such as GPS or directional sensor data, to determine a direction of acceleration. Direction of acceleration may be determined in a two-dimensional manner, such as in an X- and Y-axis direction, and may optionally not include a Z-axis direction, which may represent a change in elevation. In some embodiments, the Z-axis direction may be included. In some embodiments, the device or another computer system, such as the vehicle or a remote server, may determine, using one or more computer processors coupled to at least one memory, a first acceleration value of a device in a first direction. The device or other computer system may determine a first acceleration vector using the first acceleration value.

Block 220 of the process flow 200 may include determining an actual perpendicular value. For example, the user device may determine a vector representing an actual perpendicular value. The actual perpendicular value may represent an actual horizon location relative to an exterior of the vehicle. This is illustrated in FIG. 3.

Block 230 of the process flow 200 may include determining a perceived perpendicular value. For example, the user device may determine a vector representing a perceived perpendicular value using the acceleration value. The perceived perpendicular value may represent a horizon location perceived by the user. This is also illustrated in FIG. 3.

Figure 3:
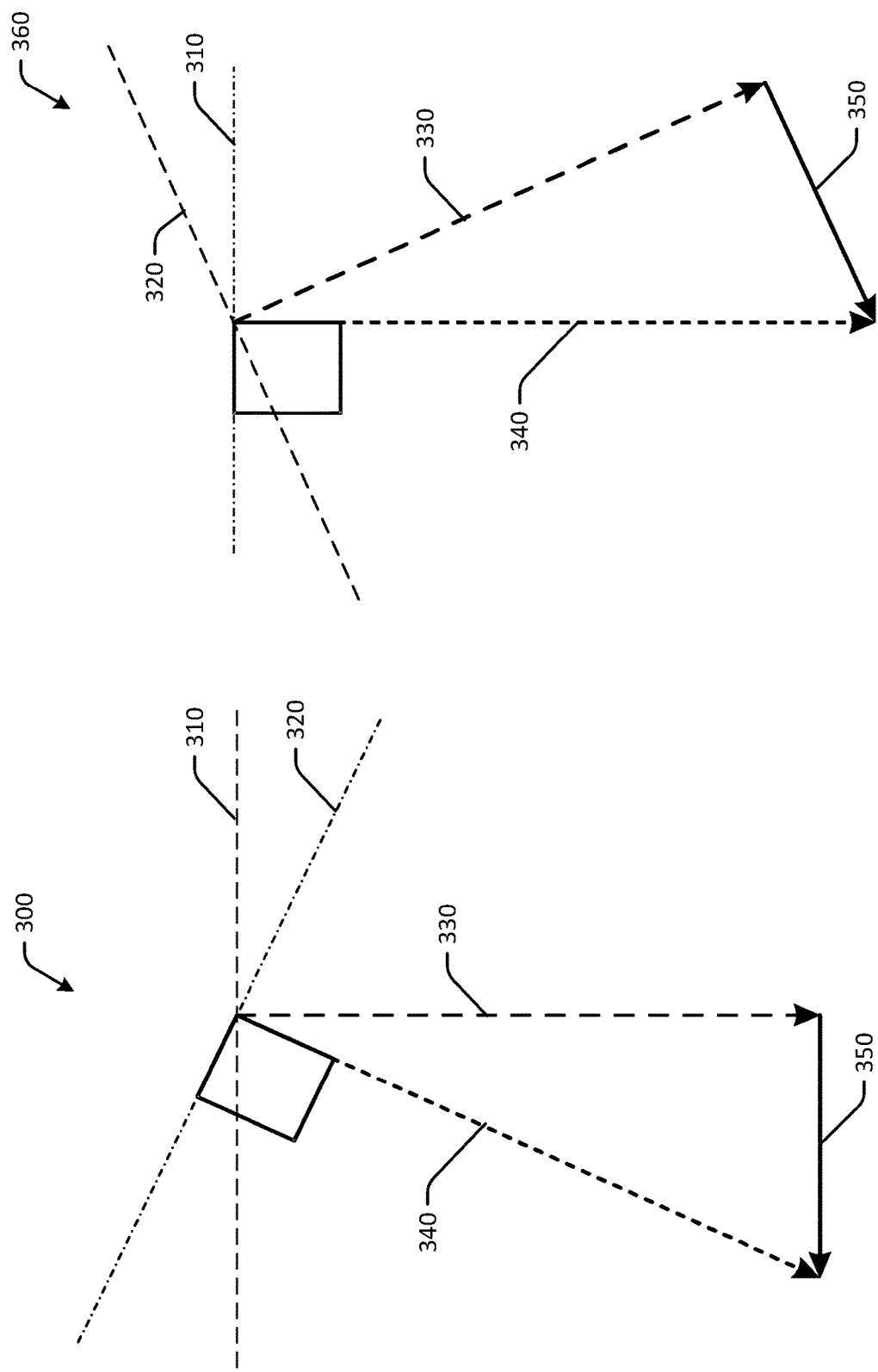
FIG. 3 is a schematic illustration of example vectors in accordance with one or more embodiments of the disclosure.

FIG. 3 schematically illustrates example vectors in accordance with one or more embodiments of the disclosure. In a first example 300, the actual exterior condition of the vehicle is illustrated. Line 310 illustrates a perceived horizon location, or a perceived perpendicular. Line 320 illustrates an actual horizon location, or an actual perpendicular. Line 350 illustrates the acceleration value represented as a vector 350. Line 330 represents an actual vertical orientation, after compensating for the acceleration vector 350. Line 340 illustrates a perceived vertical, which is determined by combining the actual vertical (line 330) and the acceleration value (line 350). As illustrated in the first example 300, the user's perception of vertical is no longer aligned an actual vertical, and may therefore be a cause motion sickness.

In a second example 360 of FIG. 3, an illustration of how a user's inner ear may perceive a vehicle interior. As illustrated, the actual horizon (line 310) is not aligned with the perceived horizon (line 320). Therefore, the inner ear of the user may comprehend the resultant force (e.g., perceived vertical line 340, etc.) to be perpendicular to the earth's surface. This perception may also be a cause of motion sickness.

Returning to FIG. 2, block 240 of the process flow 200 may include determining that a difference between the acceleration value and the perceived perpendicular value is equal to or greater than a threshold. For example, the user device or other computer system may determine whether the difference between the acceleration value and the perceived perpendicular value is greater than or equal to a sensitivity threshold. The sensitivity threshold may be a minimum magnitude of acceleration that may be detected before a graphical indicator and/or grid pattern is generated. The sensitivity threshold may therefore be used to avoid generating graphical indicators in instances where a magnitude of acceleration is not large enough to cause motion sickness. The user may therefore not be disturbed when there is no or low risk of motion sickness. The sensitivity threshold may be, for example, equivalent to 10 miles per hour of acceleration in a certain time interval (e.g., 3 seconds, etc.), or another acceleration magnitude. In some embodiments, the user device may determine that the first acceleration value is greater than or equal to a sensitivity threshold.

Block 250 of the process flow 200 may include determining a vector to correct the perceived perpendicular value using the difference. For example, the user device or other computer system may determine a vector that corrects the perceived perpendicular value to align with the actual perpendicular value based at least in part on the difference. The vector may be a clock face vector in some embodiments. The vector may be a vector in two-dimensional space. In some embodiments, the user device or other computer system may determine a baseline location of a focal point of a display of the device, and may determine a first adjusted location of the focal point of the display based at least in part on the first acceleration vector.

Block 260 of the process flow 200 may include generating a grid pattern for presentation at a device using the vector. For example, the user device or other computer system may generate the graphical indicator and/or grid pattern illustrated in FIG. 1 for presentation at a display of the device. In some embodiments, the user device, or other computer system, such as a remote server or a vehicle, may cause presentation of a graphical indicator of the first adjusted location of the focal point at the display, where the graphical indication is positioned at a second direction relative to the baseline location, and where the second direction is opposite the first direction.

In some embodiments, the user device or other computer system may determine that a first length of time has elapsed, and may cease presentation of the graphical indicator. For example, after a length of time, such as 10 seconds, the grid pattern and/or graphical indicator may no longer be presented, as the user may have adjusted their focal point and/or may not desire the view the graphical indicator or grid pattern any longer.

In some embodiments, the user device or another computer system may determine a background color of content presented at the display of the device, and may determine a color of the graphical indicator and/or grid pattern based at least in part on the background color. For example, contrasting colors may be selected for the graphical indicator or grid pattern relative to the background color presented at the device, so as to increase visibility of the graphical indicator and/or grid pattern.

Figure 4:
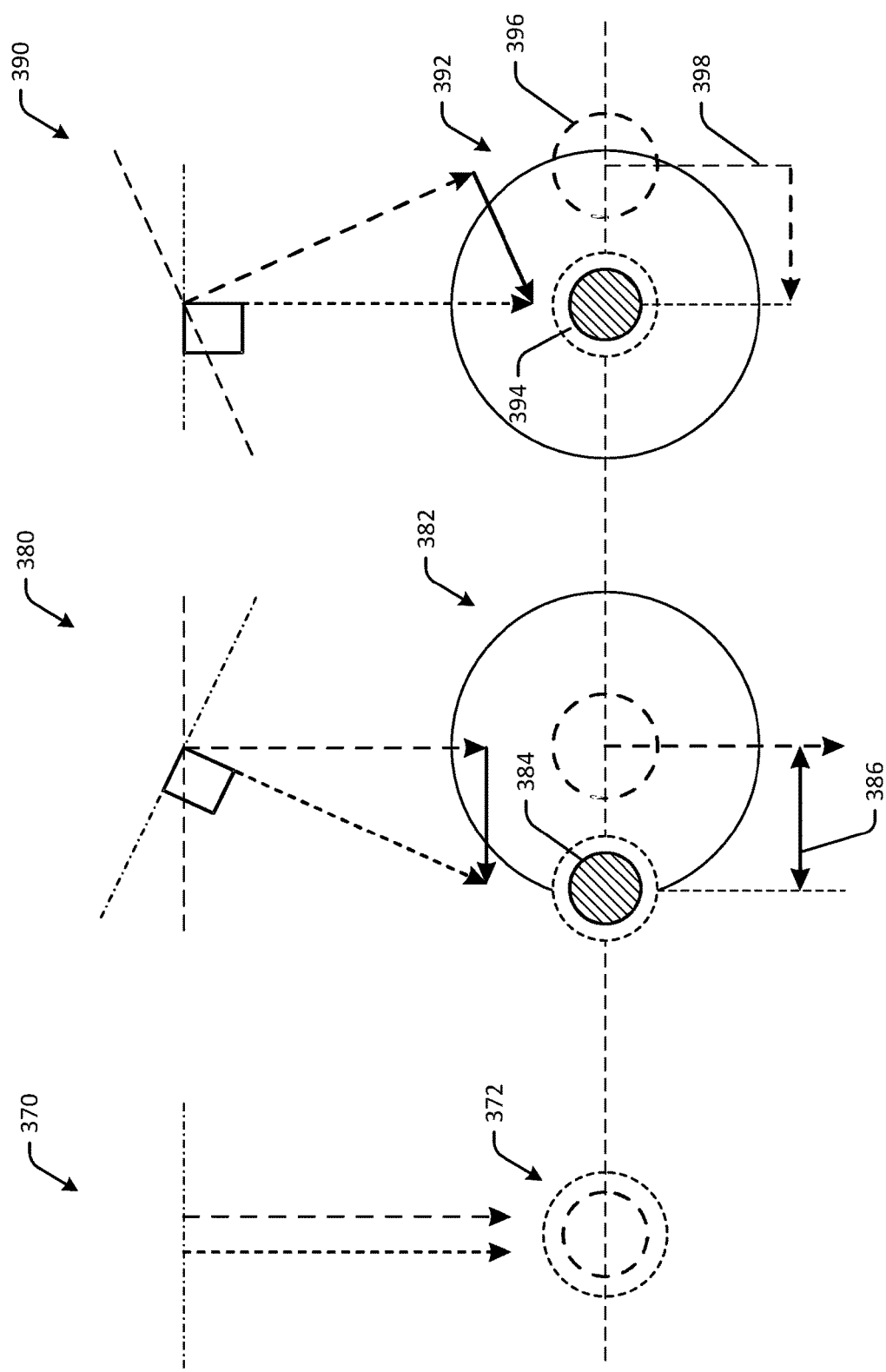
FIG. 4 is a schematic illustration of example grid pattern positioning in accordance with one or more embodiments of the disclosure.

FIG. 4 is a schematic illustration of example grid pattern positioning in accordance with one or more embodiments of the disclosure. A first example 370 may represent a stationary vehicle, in which a perceived inner ear vertical and/or inner ear perpendicular is approximately equal to an actual vertical and/or actual perpendicular. This is illustrated in FIG. 4 as the two concentric circles 372 that are substantially aligned. One of the two concentric circles 372 may be a graphical indicator. However, since the two concentric circles 372 are substantially aligned, the graphical indicator may not be generated and/or presented.

A second example 380 represents the vehicle during acceleration. During acceleration, the perceived inner ear vertical and/or inner ear perpendicular may not be equal to the actual vertical and/or actual perpendicular. There may thus be a potential cause for motion sickness. During acceleration, the two concentric circles may no longer be concentric, as illustrated in representation 382. A graphical indicator 384 representing the perceived perpendicular may be determined using the respective acceleration vector and actual perpendicular values. The magnitude of the acceleration force may be reflected by a distance 386 from which the graphical indicator 384 is displaced from a previous and/or central position.

A third example 390 represents a corrected display grid. In the third example 390, corrected positioning 392 of the graphical indicator 394 is illustrated, where the graphical indicator 394 is again concentric with the other circle. Although under no acceleration or stationary circumstances, the graphical indicator would be positioned at location 396, the acceleration of the vehicle offsets the positioning of the graphical indicator, and the graphical indicator 394 is positioned within the correct location. The correction is illustrated using line 398. As a result, the inner ear vertical and/or perpendicular may be aligned with the actual vertical and/or perpendicular, and potential motion sickness may be avoided and/or mitigated.

In some embodiments, the concentric circles may include a first graphical indicator of at least one circle formed of dashed lines, as well as a second graphical indicator. In some instances, the graphical indicator may be a baseline location of the focal point of the display of the device and may correspond to a center of the display of the device.

Figure 5:
FIG. 5 is a schematic illustration of example use case for adjusting electronic displays to mitigate motion sickness in accordance with one or more embodiments of the disclosure.

FIG. 5 is a schematic illustration of example use case 400 for adjusting electronic displays to mitigate motion sickness in accordance with one or more embodiments of the disclosure.

As illustrated in FIG. 5, a user may relatively more susceptible to motion sickness when in a head down posture, as this may cause misalignment of the user's perceived vertical and/or perpendicular orientation (as determined by the user's inner ear) relative to an actual vertical and/or perpendicular orientation. Accordingly, embodiments of the disclosure may cause the user to move their eyes upwards during acceleration in a forward direction, thereby reducing a likelihood of misalignment between the perceived and actual vertical/perpendicular orientations. For example, a user device 420 may generate a graphical indicator 410 that causes the user to look relatively upwards during forward orientation.

Figure 6:
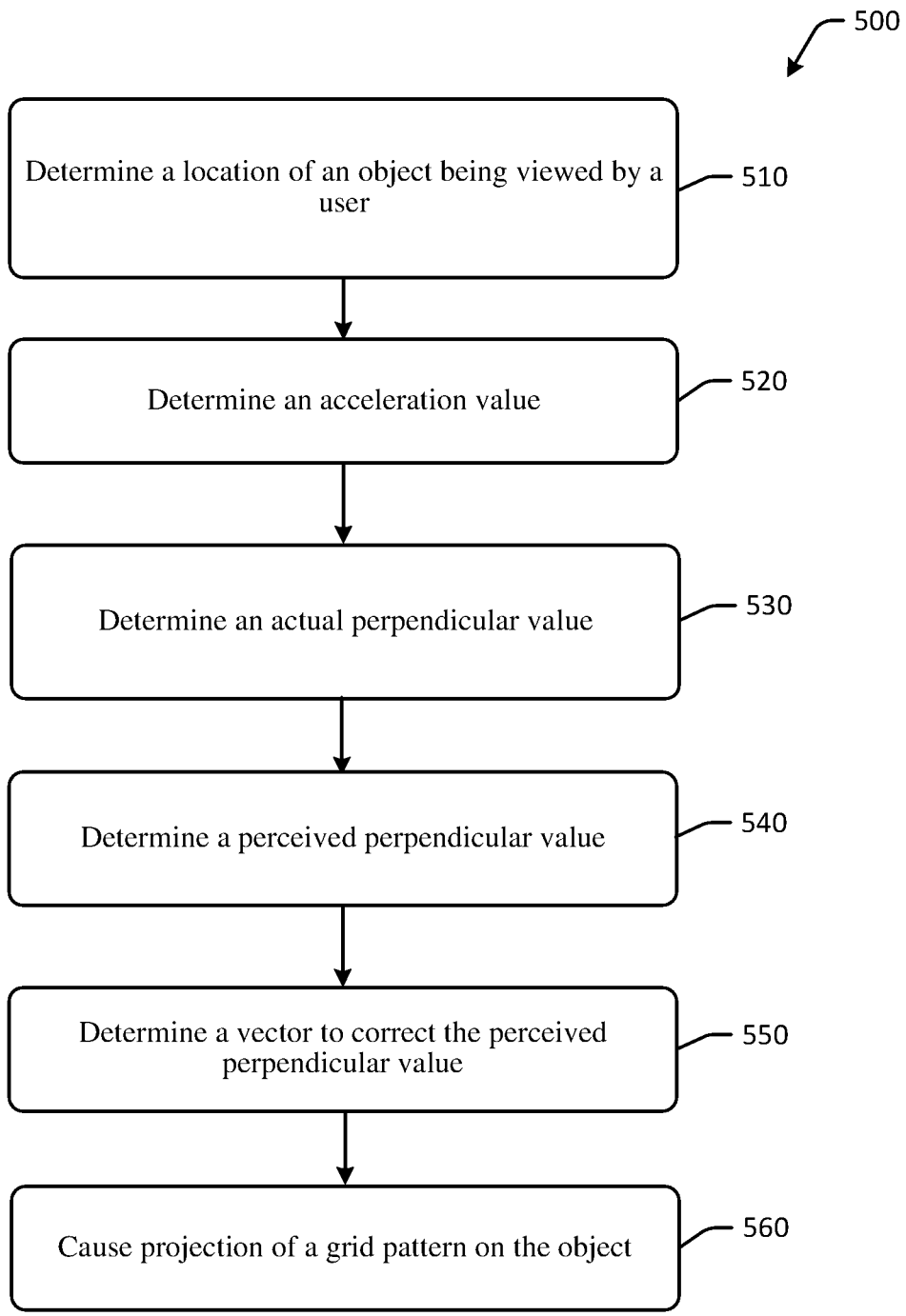
FIG. 6 is a schematic illustration of an example method for adjusting a projection system to mitigate motion sickness in accordance with one or more embodiments of the disclosure.

FIG. 6 is a schematic illustration of an example process flow 500 for adjusting a projection system to mitigate motion sickness in accordance with one or more embodiments of the disclosure. Some of the blocks of FIG. 6 represent operations that may be performed or executed by an acceleration component and/or display adjustment component of a user device or other computer system, such as a vehicle, and/or a projector system, such as that illustrated in FIG. 9. In some embodiments, the operations may be performed in a distributed manner across a plurality of computer systems. Portions of FIG. 6 are discussed in conjunction with FIG. 7.

Block 510 may include determining, by one or more computer processors coupled to at least one memory, a location of an object being viewed by a user. For example, a vehicle computer system or a user device may use one or more cameras to determine a location of an object being viewed by a user. In some embodiments, an object recognition algorithm may be used to identify objects, such as books, magazines, newspapers, etc. that may be viewed by a user. The camera may be directed towards a workstation in a vehicle, a vehicle occupant's lap, or in another direction.

Block 520 may include determining an acceleration value. For example, a user device or other computer system may determine an acceleration value using one or more inertial sensors, such as an accelerometer, that may be coupled to the user device and/or may be coupled to a computer system in communication with the user device. For example, the accelerometer may be at a vehicle that is in wired or wireless communication with the user device. The acceleration value may be an absolute value, or may include a direction. Deceleration may be represented as a negative acceleration value. In some embodiments, acceleration values may be combined with other sensor data, such as GPS or directional sensor data, to determine a direction of acceleration. Direction of acceleration may be determined in a two-dimensional manner, such as in an X- and Y-axis direction, and may optionally not include a Z-axis direction, which may represent a change in elevation. In some embodiments, the Z-axis direction may be included. In some embodiments, the device or another computer system, such as the vehicle or a remote server, may determine, using one or more computer processors coupled to at least one memory, a first acceleration value of a device in a first direction. The device or other computer system may determine a first acceleration vector using the first acceleration value.

Block 530 may include determining an actual perpendicular value. For example, the user device may determine a vector representing an actual perpendicular value. The actual perpendicular value may represent an actual horizon location relative to an exterior of the vehicle. This is illustrated in one example in FIG. 3, as discussed above.

Block 540 of the process flow 500 may include determining a perceived perpendicular value. For example, the user device may determine a vector representing a perceived perpendicular value using the acceleration value. The perceived perpendicular value may represent a horizon location perceived by the user. This is also illustrated in one example of FIG. 3, as discussed above.

Block 550 of the process flow 500 may include determining a vector to correct the perceived perpendicular value. For example, the user device or other computer system may determine a vector that corrects the perceived perpendicular value to align with the actual perpendicular value. The vector may be a clock face vector in some embodiments. The vector may be a vector in two-dimensional space. In some embodiments, the user device or other computer system may determine a baseline location of a focal point of a display of the device, and may determine a first adjusted location of the focal point of the display based at least in part on the first acceleration vector.

Block 560 of the process flow 500 may include causing projection of a grid pattern on the object. For example, the user device or other computer system may generate a grid pattern for projection using the vector. The user device or other computer system may generate the graphical indicator and/or grid pattern illustrated in FIG. 7 for projection on the object. The user device may be coupled to a projector system, or the vehicle may include a projector system, that is used to project the grid pattern on the object.

Figure 7:
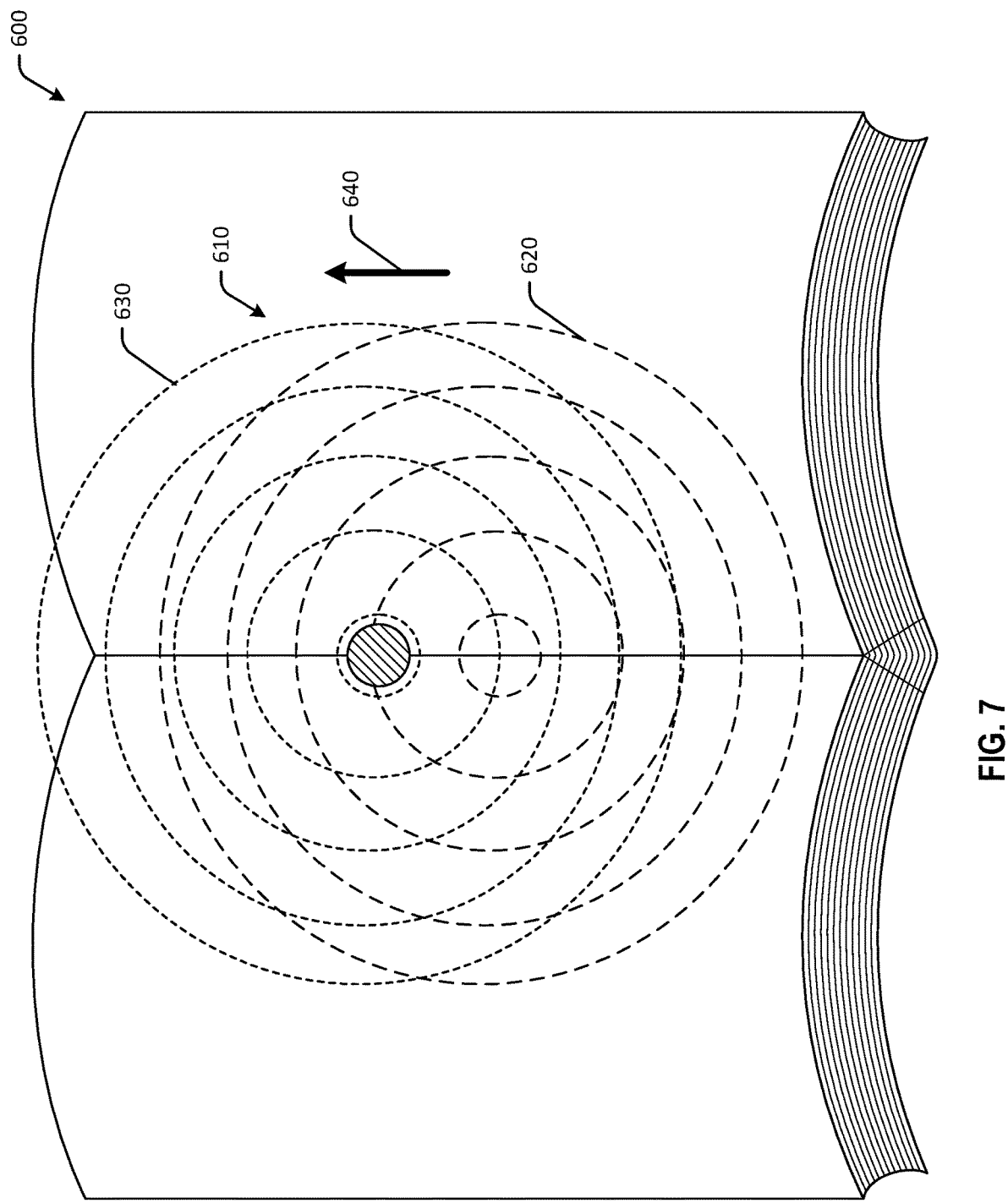
FIG. 7 is a schematic illustration of example use case for adjusting a projection system to mitigate motion sickness in accordance with one or more embodiments of the disclosure.

FIG. 7 is a schematic illustration of example use case for adjusting a projection system to mitigate motion sickness in accordance with one or more embodiments of the disclosure.

In FIG. 7, a user may be reading a book 600 that is positioned on the user's lap. The system may determine the location of the book 600, and using the acceleration vector calculated for the vehicle and/or user device, the system may cause one or more grid patterns 610 to be projected on the book. A baseline grid 620 for a stationary vehicle is illustrated for illustrative purposes, and a projected grid pattern 630 that compensates for the perceived inner ear vertical may be projected on the book. As illustrated, the projected grid pattern 630 may be moved forward in direction 640 until it matches the calculated perceived vertical of the user's inner ear to align the perceived motion with the visual motion to reduce or eliminate motion sickness. The change in location of the graphical indicator may be a result of the magnitude and direction of acceleration.

Figure 8:
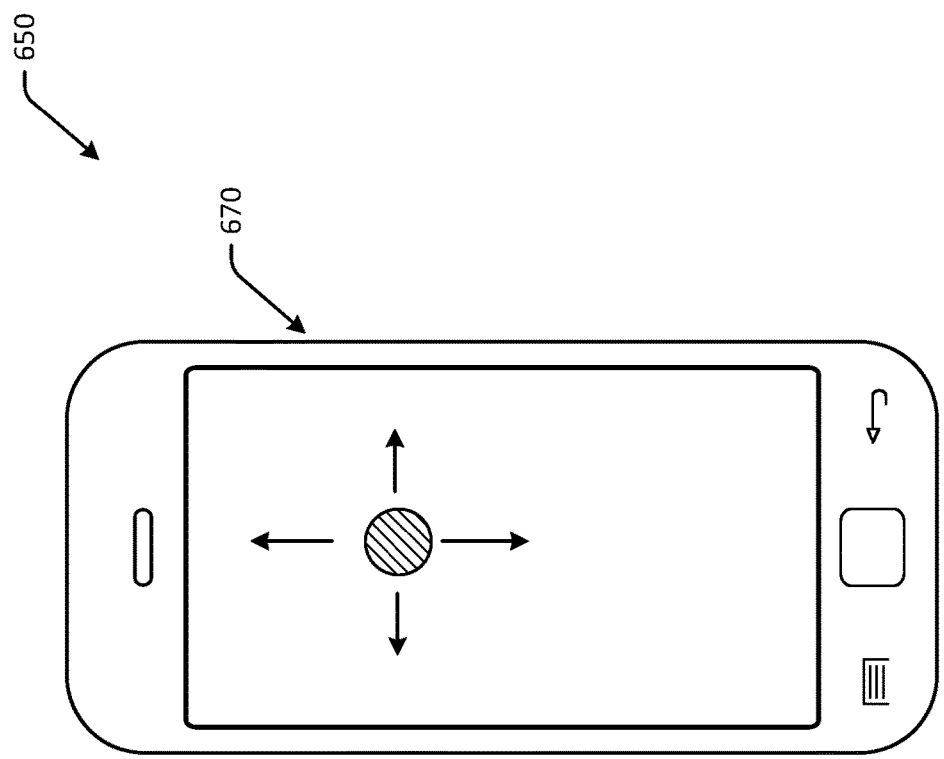
FIG. 8 is a schematic illustration of example user interfaces for adjusting electronic displays to mitigate motion sickness in accordance with one or more embodiments of the disclosure.
Figure 8:
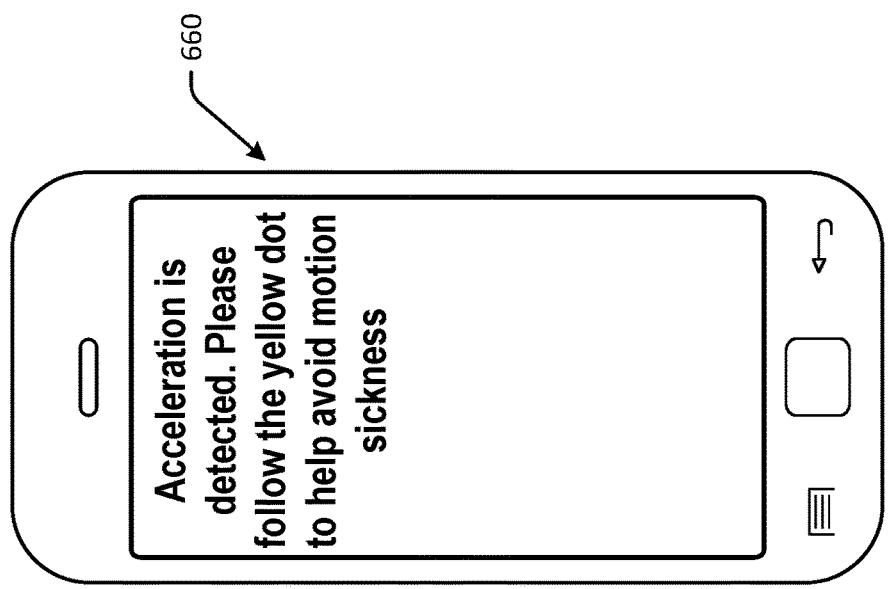

FIG. 8 is a schematic illustration of example user interfaces 650 for adjusting electronic displays to mitigate motion sickness in accordance with one or more embodiments of the disclosure.

At a first user interface 660, a user device may be used for consuming content. An accelerometer of the user device may be used to detect acceleration of the user device. When acceleration above the sensitivity threshold is detected, a message indicating the anti-motion sickness software activation may be presented, as illustrated in FIG. 8. At a second user interface 670, the graphical indicator may be generated and presented for the user to help avoid motion sickness.

Figure 9:
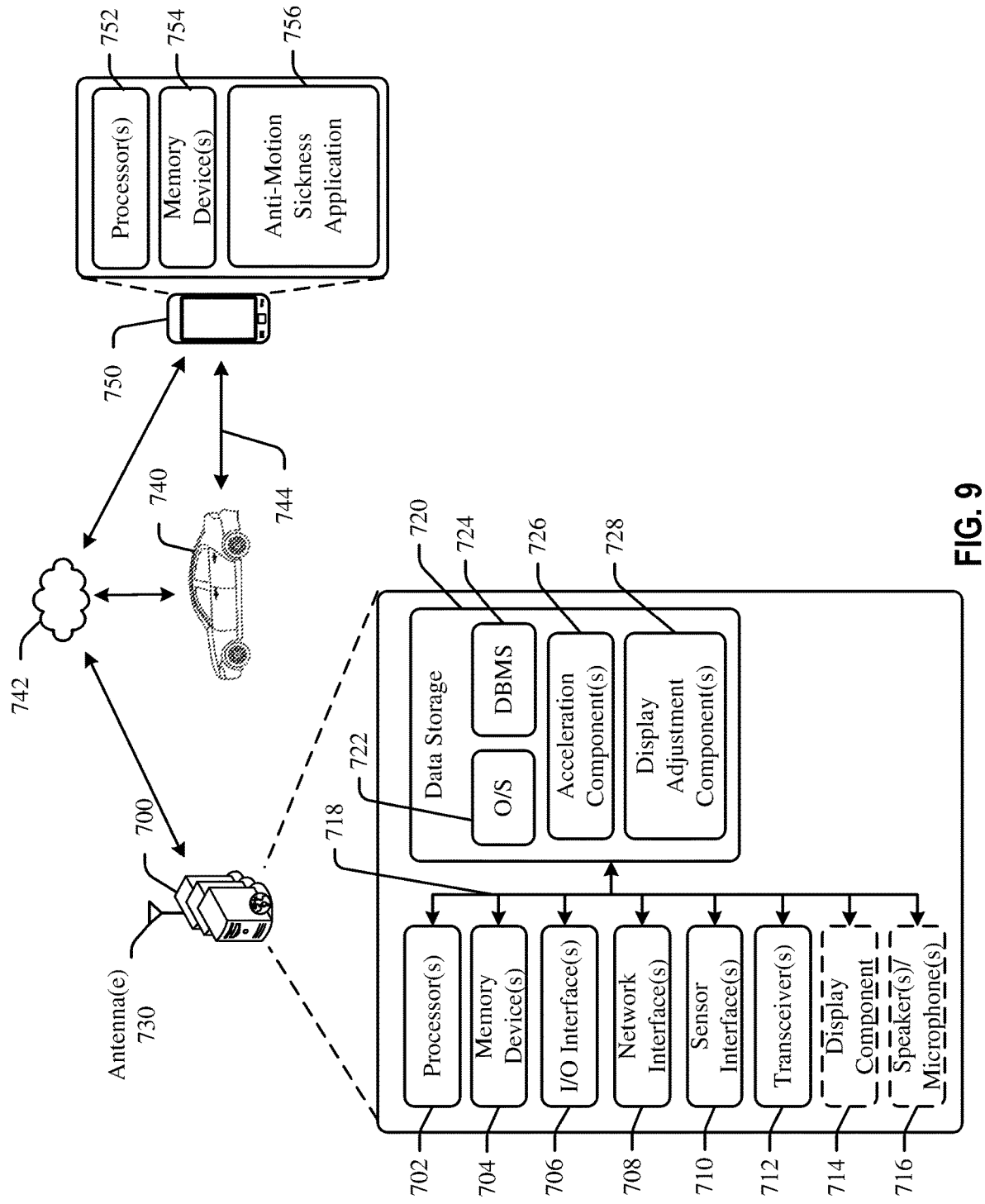
FIG. 9 is a schematic illustration of an example system architecture in accordance with one or more embodiments of the disclosure.

FIG. 9 is a schematic illustration of an example system architecture in accordance with one or more embodiments of the disclosure. The system may include one or more server(s) 700, one or more vehicles 740, and/or one or more user devices 750. The server 700, vehicle 740, and/or user device 750 may be in communication via one or more networks 742. The illustrated server 700, vehicle 740, and/or user device 750 may be configured to implement one or more of the operations and/or processes discussed herein, such as the processes of FIGS. 2 and/or 6. Some or all of the illustrated individual components may be optional and/or different in various embodiments. In some embodiments, at least one of the servers or devices described with respect to FIGS. 1 and 2 may be located at an autonomous vehicle.

The server 700 may be in communication with the autonomous vehicle 740, and one or more user devices 750. The autonomous vehicle 740 may be in communication with the user device 750.

The server 700, the autonomous vehicle 740, and/or the user device 750 may be configured to communicate via one or more networks 742. The autonomous vehicle 740 may additionally be in wireless communication 744 with the user device 750 via a connection protocol such as Bluetooth or Near Field Communication. Such network(s) 742 may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the server 700 may include one or more processors (processor(s)) 702, one or more memory devices 704 (also referred to herein as memory 704), one or more input/output (I/O) interface(s) 706, one or more network interface(s) 708, one or more sensor(s) or sensor interface(s) 710, one or more transceiver(s) 712, one or more optional display components 714, one or more optional camera(s)/microphone(s) 716, and data storage 720. The server 700 may further include one or more bus(es) 718 that functionally couple various components of the server 700. The server 700 may further include one or more antenna(e) 730 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) 718 may include at least one of a system bus, a memory bus, an address bus, or a message bus, and may permit the exchange of information (e.g., data (including computer-executable code), signaling, etc.) between various components of the server 700. The bus(es) 718 may include, without limitation, a memory bus or a memory controller, a peripheral bus, an accelerated graphics port, and so forth. The bus(es) 718 may be associated with any suitable bus architecture.

The memory 704 of the server 700 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

The data storage 720 may include removable storage and/or non-removable storage including, but not limited to, magnetic storage, optical disk storage, and/or tape storage. The data storage 720 may provide non-volatile storage of computer-executable instructions and other data.

The data storage 720 may store computer-executable code, instructions, or the like that may be loadable into the memory 704 and executable by the processor(s) 702 to cause the processor(s) 702 to perform or initiate various operations. The data storage 720 may additionally store data that may be copied to the memory 704 for use by the processor(s) 702 during the execution of the computer-executable instructions. More specifically, the data storage 720 may store one or more operating systems (O/S) 722; one or more database management systems (DBMS) 724; and one or more program module(s), applications, engines, computer-executable code, scripts, or the like such as, for example, one or more acceleration component(s) 726 and/or one or more display adjustment component(s) 728. Some or all of these component(s) may be sub-component(s). Any of the components depicted as being stored in the data storage 720 may include any combination of software, firmware, and/or hardware. The software and/or firmware may include computer-executable code, instructions, or the like that may be loaded into the memory 704 for execution by one or more of the processor(s) 702. Any of the components depicted as being stored in the data storage 720 may support functionality described in reference to corresponding components named earlier in this disclosure.

The processor(s) 702 may be configured to access the memory 704 and execute the computer-executable instructions loaded therein. For example, the processor(s) 702 may be configured to execute the computer-executable instructions of the various program module(s), applications, engines, or the like of the server 700 to cause or facilitate various operations to be performed in accordance with one or more embodiments of the disclosure. The processor(s) 702 may include any suitable processing unit capable of accepting data as input, processing the input data in accordance with stored computer-executable instructions, and generating output data. The processor(s) 702 may include any type of suitable processing unit.

Referring now to functionality supported by the various program component(s) depicted in FIG. 9, the acceleration component(s) 726 may include computer-executable instructions, code, or the like that responsive to execution by one or more of the processor(s) 702 may perform one or more blocks of the process flows 200 and process flow 500 and/or functions including, but not limited to, determining accelerometer sensor output, generating acceleration vectors, calculating acceleration values, and the like. The acceleration component(s) 726 may be in communication with the autonomous vehicle 740, user device 750, another server, and/or other components.

The display adjustment component(s) 728 may include computer-executable instructions, code, or the like that responsive to execution by one or more of the processor(s) 702 may perform one or more blocks of the process flows 200 and process flow 500 and/or functions including, but not limited to, determining background colors, determining graphical indicators and colors, generating graphical indicators and grid patterns, causing presentation of graphical indicators, and the like. In some embodiments, causing presentation of graphical indicators may include generation (by a remote computing system, and in some instances sending) of a message that indicates a certain direction relative to a baseline, which may be received by a device and processed to generate the display feature.

The display adjustment component(s) 728 may be in communication with the autonomous vehicle 740 (such as a projector system of the autonomous vehicle or the user device), user device 750, another server, and/or other components.

Referring now to other illustrative components depicted as being stored in the data storage 720, the O/S 722 may be loaded from the data storage 720 into the memory 704 and may provide an interface between other application software executing on the server 700 and the hardware resources of the server 700.

The DBMS 724 may be loaded into the memory 704 and may support functionality for accessing, retrieving, storing, and/or manipulating data stored in the memory 704 and/or data stored in the data storage 720. The DBMS 724 may use any of a variety of database models (e.g., relational model, object model, etc.) and may support any of a variety of query languages.

Referring now to other illustrative components of the server 700, the input/output (I/O) interface(s) 706 may facilitate the receipt of input information by the server 700 from one or more I/O devices as well as the output of information from the server 700 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. The I/O interface(s) 706 may also include a connection to one or more of the antenna(e) 730 to connect to one or more networks via a wireless local area network (WLAN) (such as Wi-Fi) radio, Bluetooth, ZigBee, and/or a wireless network radio, such as a radio capable of communication with a wireless communication network such as a Long Term Evolution (LTE) network, WiMAX network, 3G network, a ZigBee network, etc.

The server 700 may further include one or more network interface(s) 708 via which the server 700 may communicate with any of a variety of other systems, platforms, networks, devices, and so forth. The network interface(s) 708 may enable communication, for example, with one or more wireless routers, one or more host servers, one or more web servers, and the like via one or more networks.

The sensor(s)/sensor interface(s) 710 may include or may be capable of interfacing with any suitable type of sensing device such as, for example, inertial sensors, force sensors, thermal sensors, photocells, and so forth.

The display component(s) 714 may include one or more display layers, such as LED or LCD layers, touch screen layers, protective layers, and/or other layers. The optional camera(s) 716 may be any device configured to capture ambient light or images. The optional microphone(s) 716 may be any device configured to receive analog sound input or voice data. The microphone(s) 716 may include microphones used to capture sound.

It should be appreciated that the program module(s), applications, computer-executable instructions, code, or the like depicted in FIG. 9 as being stored in the data storage 720 are merely illustrative and not exhaustive and that processing described as being supported by any particular module may alternatively be distributed across multiple module(s) or performed by a different module.

It should further be appreciated that the server 700 may include alternate and/or additional hardware, software, or firmware components beyond those described or depicted without departing from the scope of the disclosure.

The user device 750 may include one or more computer processor(s) 752, one or more memory devices 754, and one or more applications, such as an anti-motion sickness application 756. Other embodiments may include different components.

The processor(s) 752 may be configured to access the memory 754 and execute the computer-executable instructions loaded therein. For example, the processor(s) 752 may be configured to execute the computer-executable instructions of the various program module(s), applications, engines, or the like of the device to cause or facilitate various operations to be performed in accordance with one or more embodiments of the disclosure. The processor(s) 752 may include any suitable processing unit capable of accepting data as input, processing the input data in accordance with stored computer-executable instructions, and generating output data. The processor(s) 752 may include any type of suitable processing unit.

The memory 754 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

Referring now to functionality supported by the user device 750, the anti-motion sickness application 756 may be a mobile application executable by the processor 752 that can be used to present the graphical indicators and/or grid pattern, determine accelerometer output, determine acceleration vectors, and so forth. In addition, the user device 750 may communicate with the autonomous vehicle 740 via the network 742 and/or a direct connection, which may be a wireless or wired connection. The user device 750 may include a camera, projector system, and/or other components.

It should be appreciated that the program module(s), applications, computer-executable instructions, code, or the like depicted in FIG. 9 as being stored in the data storage 720 are merely illustrative and not exhaustive and that processing described as being supported by any particular module may alternatively be distributed across multiple module(s) or performed by a different module.

It should further be appreciated that the server 700 may include alternate and/or additional hardware, software, or firmware components beyond those described or depicted without departing from the scope of the disclosure.

One or more operations of the methods, process flows, and use cases of FIGS. 1-9 may be performed by a device having the illustrative configuration depicted in FIG. 9, or more specifically, by one or more engines, program module(s), applications, or the like executable on such a device. It should be appreciated, however, that such operations may be implemented in connection with numerous other device configurations.

The operations described and depicted in the illustrative methods and process flows of FIGS. 1-9 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 1-9 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

According to an aspect of the disclosure, a method may include determining, by one or more computer processors coupled to at least one memory, a first acceleration value of a device in a first direction, determining a first acceleration vector using the first acceleration value, and determining a baseline location of a focal point of a display of the device. The method may include determining a first adjusted location of the focal point of the display based at least in part on the first acceleration vector, and causing presentation of a graphical indicator of the first adjusted location of the focal point at the display, wherein the graphical indication is positioned at a second direction relative to the baseline location, and wherein the second direction is opposite the first direction. The method may include determining that the first acceleration value is greater than or equal to a sensitivity threshold. The method may include determining that a first length of time has elapsed, and ceasing presentation of the graphical indicator. The method may include determining a background color of content presented at the display, and determining a color of the graphical indicator based at least in part on the background color. The method may include, where the graphical indicator is a first graphical indicator, generating a grid pattern about the first graphical indicator, wherein the grid pattern comprises at least one circle formed of dashed lines, causing presentation of the grid pattern for a first length of time, and causing presentation of a second graphical indicator corresponding to the baseline location for a second length of time that is less than the first length of time. The method may include determining that the first length of time has elapsed, and causing the at least one circle to be presented with a solid line. The baseline location of the focal point of the display of the device may correspond to a center of the display of the device. The first acceleration value may be received from an accelerometer of the device.

According to another aspect of this disclosure, a system may include at least one memory comprising computer-executable instructions, and one or more computer processors configured to access the at least one memory and execute the computer-executable instructions to: determine a first acceleration value of the device in a first direction, determine a first acceleration vector using the first acceleration value, determine a baseline location of a focal point of a display of the device, determine a first adjusted location of the focal point of the display based at least in part on the first acceleration vector, and cause presentation of a graphical indicator of the first adjusted location of the focal point at the display, wherein the graphical indication is positioned at a second direction relative to the baseline location, and wherein the second direction is opposite the first direction. The one or more computer processors may be further configured to access the at least one memory and execute the computer-executable instructions to determine that the first acceleration value is greater than or equal to a sensitivity threshold. The one or more computer processors may be further configured to access the at least one memory and execute the computer-executable instructions to determine that a first length of time has elapsed, and cease presentation of the graphical indicator. The one or more computer processors may be further configured to access the at least one memory and execute the computer-executable instructions to determine a background color of content presented at the display, and determine a color of the graphical indicator based at least in part on the background color. The one or more computer processors may be further configured to access the at least one memory and execute the computer-executable instructions to, where the graphical indicator is a first graphical indicator, generate a grid pattern about the first graphical indicator, wherein the grid pattern comprises at least one circle formed of dashed lines, cause presentation of the grid pattern for a first length of time, and cause presentation of a second graphical indicator corresponding to the baseline location for a second length of time that is less than the first length of time. The one or more computer processors may be further configured to access the at least one memory and execute the computer-executable instructions to determine that the first length of time has elapsed, and cause the at least one circle to be presented with a solid line. The baseline location of the focal point of the display of the device may correspond to a center of the display of the device. The first acceleration value may be received from an accelerometer of the device.

According to another aspect of this disclosure, a method may include determining a first acceleration value in a first direction, determining a first acceleration vector using the first acceleration value, determining a baseline location of a focal point of an object, determining a first adjusted location of the focal point of the object based at least in part on the first acceleration vector, and causing presentation of a graphical indicator of the first adjusted location of the focal point on the object using a projector system. The graphical indication may be positioned at a second direction relative to the baseline location, and the second direction may be opposite the first direction. The system and the projector system may be located at a vehicle. The first acceleration value may be received from an accelerometer of a device associated with the vehicle.

Example embodiments may include one or more of the following:

Example 1 may include a method comprising: determining, by one or more computer processors coupled to at least one memory, a first acceleration value of a device in a first direction; determining a first acceleration vector using the first acceleration value; determining a baseline location of a focal point of a display of the device; determining a first adjusted location of the focal point of the display based at least in part on the first acceleration vector; and causing presentation of a graphical indicator of the first adjusted location of the focal point at the display, wherein the graphical indication is positioned at a second direction relative to the baseline location, and wherein the second direction is opposite the first direction.

Example 2 may include the method of example 1 and/or some other example herein, further comprising: determining that the first acceleration value is greater than or equal to a sensitivity threshold.

Example 3 may include the method of example 1 and/or some other example herein, further comprising: determining that a first length of time has elapsed; and ceasing presentation of the graphical indicator.

Example 4 may include the method of example 1 and/or some other example herein, further comprising: determining a background color of content presented at the display; and determining a color of the graphical indicator based at least in part on the background color.

Example 5 may include the method of example 1 and/or some other example herein, wherein the graphical indicator is a first graphical indicator, the method further comprising: generating a grid pattern about the first graphical indicator, wherein the grid pattern comprises at least one circle formed of dashed lines; causing presentation of the grid pattern for a first length of time; and causing presentation of a second graphical indicator corresponding to the baseline location for a second length of time that is less than the first length of time.

Example 6 may include the method of example 5 and/or some other example herein, further comprising: determining that the first length of time has elapsed; and causing the at least one circle to be presented with a solid line.

Example 7 may include the method of example 1 and/or some other example herein, wherein the baseline location of the focal point of the display of the device corresponds to a center of the display of the device.

Example 8 may include the method of example 1 and/or some other example herein, wherein the first acceleration value is received from an accelerometer of the device.

Example 9 may include a device comprising: at least one memory storing computer-executable instructions; and one or more computer processors coupled to the at least one memory and configured to execute the computer-executable instructions to: determine a first acceleration value of the device in a first direction; determine a first acceleration vector using the first acceleration value; determine a baseline location of a focal point of a display of the device; determine a first adjusted location of the focal point of the display based at least in part on the first acceleration vector; and cause presentation of a graphical indicator of the first adjusted location of the focal point at the display, wherein the graphical indication is positioned at a second direction relative to the baseline location, and wherein the second direction is opposite the first direction.

Example 10 may include the device of example 9 and/or some other example herein, wherein the one or more computer processors are further configured to execute the computer-executable instructions to: determine that the first acceleration value is greater than or equal to a sensitivity threshold.

Example 11 may include the device of example 9 and/or some other example herein, wherein the one or more computer processors are further configured to execute the computer-executable instructions to: determine that a first length of time has elapsed; and cease presentation of the graphical indicator.

Example 12 may include the device of example 9 and/or some other example herein, wherein the one or more computer processors are further configured to execute the computer-executable instructions to: determine a background color of content presented at the display; and determine a color of the graphical indicator based at least in part on the background color.

Example 13 may include the device of example 9 and/or some other example herein, wherein the graphical indicator is a first graphical indicator and wherein the one or more computer processors are further configured to execute the computer-executable instructions to: generate a grid pattern about the first graphical indicator, wherein the grid pattern comprises at least one circle formed of dashed lines; cause presentation of the grid pattern for a first length of time; and cause presentation of a second graphical indicator corresponding to the baseline location for a second length of time that is less than the first length of time.

Example 14 may include the device of example 13 and/or some other example herein, wherein the one or more computer processors are further configured to execute the computer-executable instructions to: determine that the first length of time has elapsed; and cause the at least one circle to be presented with a solid line.

Example 15 may include the device of example 9 and/or some other example herein, wherein the baseline location of the focal point of the display of the device corresponds to a center of the display of the device.

Example 16 may include the device of example 9 and/or some other example herein, wherein the first acceleration value is received from an accelerometer of the device.

Example 17 may include a system comprising: one or more memory devices comprising computer-executable instructions; and at least one computer processor coupled to the one or more memory devices and configured to execute the computer-executable instructions to: determine a first acceleration value in a first direction; determine a first acceleration vector using the first acceleration value; determine a baseline location of a focal point of an object; determine a first adjusted location of the focal point of the object based at least in part on the first acceleration vector; and cause presentation of a graphical indicator of the first adjusted location of the focal point on the object using a projector system.

Example 18 may include the system of example 17 and/or some other example herein, wherein the graphical indication is positioned at a second direction relative to the baseline location, and wherein the second direction is opposite the first direction.

Example 19 may include the system of example 17 and/or some other example herein, wherein the system and the projector system is located at a vehicle.

Example 20 may include the system of example 19 and/or some other example herein, wherein the first acceleration value is received from an accelerometer of a device associated with the vehicle.

What is claimed is:

1. A method comprising:
   determining, by one or more computer processors coupled to at least one memory, a baseline location of a focal point of a display of a device;
   determining a first acceleration value of the device in a first direction relative to the baseline location;
   determining a first acceleration vector using the first acceleration value;
   determining a first adjusted location of the focal point of the display based on the first acceleration vector; and
   causing presentation of a graphical indicator of the first adjusted location of the focal point on the display, wherein a direction of the first adjusted location relative to the baseline location is opposite to the first direction relative to the baseline location.

2. The method of claim 1, further comprising:
   determining that the first acceleration value is greater than or equal to a sensitivity threshold, wherein causing presentation of the graphical indicator is further based on the determination that the first acceleration value is greater than or equal to the sensitivity threshold.

3. The method of claim 1, further comprising:
   determining that a first length of time has elapsed since presentation of the graphical indicator; and
   ceasing presentation of the graphical indicator.

4. The method of claim 1, further comprising:
determining a background color of content presented on the display; and
determining a color of the graphical indicator based at least in part on the background color.

5. The method of claim 1, wherein the graphical indicator is a first graphical indicator, the method further comprising:
generating a grid pattern about the first graphical indicator, wherein the grid pattern comprises at least one circle formed of dashed lines;
causing presentation of the grid pattern for a first length of time; and
causing presentation of a second graphical indicator corresponding to the baseline location for a second length of time that is less than the first length of time.

6. The method of claim 5, further comprising:
determining that the first length of time has elapsed; and
causing the at least one circle to be presented with a solid line.

7. The method of claim 1, wherein the baseline location of the focal point of the display of the device corresponds to a center of the display of the device.

8. The method of claim 1, wherein the first acceleration value is received from an accelerometer of the device.

9. A device comprising:
at least one memory storing computer-executable instructions; and
one or more computer processors coupled to the at least one memory and configured to execute the computer-executable instructions to:
determine a baseline location of a focal point of a display of the device;
determine a first acceleration value of the device in a first direction relative to the baseline location;
determine a first acceleration vector using the first acceleration value;
determine a first adjusted location of the focal point of the display based on the first acceleration vector; and
cause presentation of a graphical indicator of the first adjusted location of the focal point on the display, wherein a direction of the first adjusted location relative to the baseline location is opposite to the first direction relative to the baseline location.

10. The device of claim 9, wherein the one or more computer processors are further configured to execute computer-executable instructions to:
determine that the first acceleration value is greater than or equal to a sensitivity threshold, wherein causing presentation of the graphical indicator is further based on the determination that the first acceleration value is greater than or equal to the sensitivity threshold.

11. The device of claim 9, wherein the one or more computer processors are further configured to execute the computer-executable instructions to:
determine that a first length of time has elapsed since presentation of the graphical indicator; and
cease presentation of the graphical indicator.

12. The device of claim 9, wherein the one or more computer processors are further configured to execute the computer-executable instructions to:
determine a background color of content presented at the display; and
determine a color of the graphical indicator based at least in part on the background color.

13. The device of claim 9, wherein the graphical indicator is a first graphical indicator and wherein the one or more computer processors are further configured to execute the computer-executable instructions to:
generate a grid pattern about the first graphical indicator, wherein the grid pattern comprises at least one circle formed of dashed lines;
cause presentation of the grid pattern for a first length of time; and
cause presentation of a second graphical indicator corresponding to the baseline location for a second length of time that is less than the first length of time.

14. The device of claim 13, wherein the one or more computer processors are further configured to execute the computer-executable instructions to:
determine that the first length of time has elapsed; and
cause the at least one circle to be presented with a solid line.

15. The device of claim 9, wherein the baseline location of the focal point of the display of the device corresponds to a center of the display of the device.

16. The device of claim 9, wherein the first acceleration value is received from an accelerometer of the device.

17. A system comprising:
one or more memory devices comprising computer-executable instructions; and
at least one computer processor coupled to the one or more memory devices and configured to execute the computer-executable instructions to:
determine a baseline location of a focal point of a display of the device;
determine a first acceleration value of the device in a first direction relative to the baseline location;
determine a first acceleration vector using the first acceleration value;
determine a first adjusted location of the focal point of the display based on the first acceleration vector; and
cause presentation of a graphical indicator of the first adjusted location of the focal point on the display.

18. The system of claim 17, wherein the graphical indication is positioned at a second direction relative to the baseline location, and wherein the second direction is opposite the first direction.

19. The system of claim 17, wherein the first acceleration value is received from an accelerometer of a device associated with a vehicle.

* * * * *